(12) United States Patent
Yamaguchi et al.

(10) Patent No.: US 10,952,596 B2
(45) Date of Patent: Mar. 23, 2021

(54) MEDICAL IMAGE PROCESSING DEVICE AND IMAGE PROCESSING METHOD

(71) Applicant: SONY CORPORATION, Tokyo (JP)

(72) Inventors: Kenta Yamaguchi, Kanagawa (JP); Yasuaki Takahashi, Kanagawa (JP); Kenji Ikeda, Kanagawa (JP); Tomoyuki Hirayama, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 57 days.

(21) Appl. No.: 16/324,961

(22) PCT Filed: Jul. 21, 2017

(86) PCT No.: PCT/JP2017/026400
§ 371 (c)(1),
(2) Date: Feb. 12, 2019

(87) PCT Pub. No.: WO2018/047478
PCT Pub. Date: Mar. 15, 2018

(65) Prior Publication Data
US 2019/0183322 A1 Jun. 20, 2019

(30) Foreign Application Priority Data

Sep. 6, 2016 (JP) .............................. JP2016-173378

(51) Int. Cl.
*A61B 1/045* (2006.01)
*A61B 1/00* (2006.01)
(Continued)

(52) U.S. Cl.
CPC ............ *A61B 1/045* (2013.01); *A61B 1/0005* (2013.01); *A61B 1/00009* (2013.01);
(Continued)

(58) Field of Classification Search
CPC ... A61B 1/045; A61B 1/0005; A61B 1/00009; A61B 2090/368; A61B 1/05;
(Continued)

(56) References Cited

U.S. PATENT DOCUMENTS

2013/0307952 A1* 11/2013 Ishihara ............... A61B 5/0071
348/68
2015/0238086 A1* 8/2015 Saito .................... A61B 1/0638
600/339
(Continued)

FOREIGN PATENT DOCUMENTS

| CN | 103081456 A | 5/2013 |
| CN | 103327880 A | 9/2013 |

(Continued)

OTHER PUBLICATIONS

International Search Report and Written Opinion of PCT Application No. PCT/JP2017/026400, dated Oct. 3, 2017, 10 pages of ISRWO.

*Primary Examiner* — Said M Elnoubi
(74) *Attorney, Agent, or Firm* — Chip Law Group

(57) ABSTRACT

There is provided a medical image processing device and an image processing method. The medical image processing device includes an acquisition unit that acquires application information indicating an application related to a display, and an image processing unit that performs image processing based on the application information to acquire an output image.

19 Claims, 16 Drawing Sheets

(51) Int. Cl.
  *G16H 30/40* (2018.01)
  *A61B 90/00* (2016.01)
  *A61B 1/05* (2006.01)
(52) U.S. Cl.
  CPC .............. *G16H 30/40* (2018.01); *A61B 1/05* (2013.01); *A61B 2090/368* (2016.02)
(58) Field of Classification Search
  CPC ........ A61B 2034/254; A61B 2034/258; A61B 2090/372; A61B 2090/365; A61B 90/36; A61B 2090/371; A61B 2017/00216; G16H 30/40; G16H 20/40; G16H 40/63
  See application file for complete search history.

(56) References Cited

U.S. PATENT DOCUMENTS

| | | | |
|---|---|---|---|
| 2016/0154620 A1* | 6/2016 | Tsuda | G06F 3/1423 345/633 |
| 2017/0046842 A1 | 2/2017 | Yamaguchi | |

FOREIGN PATENT DOCUMENTS

| | | | | |
|---|---|---|---|---|
| CN | 104298344 A | 1/2015 | | |
| EP | 2656774 A1 | 10/2013 | | |
| JP | 09-005643 A | 1/1997 | | |
| JP | 2004-041778 A | 2/2004 | | |
| JP | 2010-220755 A | 10/2010 | | |
| JP | 2015-188566 A | 11/2015 | | |
| JP | 2015-228954 A | 12/2015 | | |
| JP | 2016-036592 A | 3/2016 | | |
| JP | 2016-115965 A | 6/2016 | | |
| WO | 2011/152489 A1 | 12/2011 | | |
| WO | 2012/033200 A1 | 3/2012 | | |
| WO | WO-2012033200 A1 * | 3/2012 | ............. | H04N 5/345 |
| WO | 2012/105445 A1 | 8/2012 | | |
| WO | 2015/105445 A1 | 8/2012 | | |
| WO | 2015/008470 A2 | 1/2015 | | |
| WO | 2015/186339 A1 | 12/2015 | | |
| WO | 2016/092950 A1 | 6/2016 | | |
| WO | WO-2016092950 A1 * | 6/2016 | ............... | G09G 5/00 |

* cited by examiner

FIG. 5
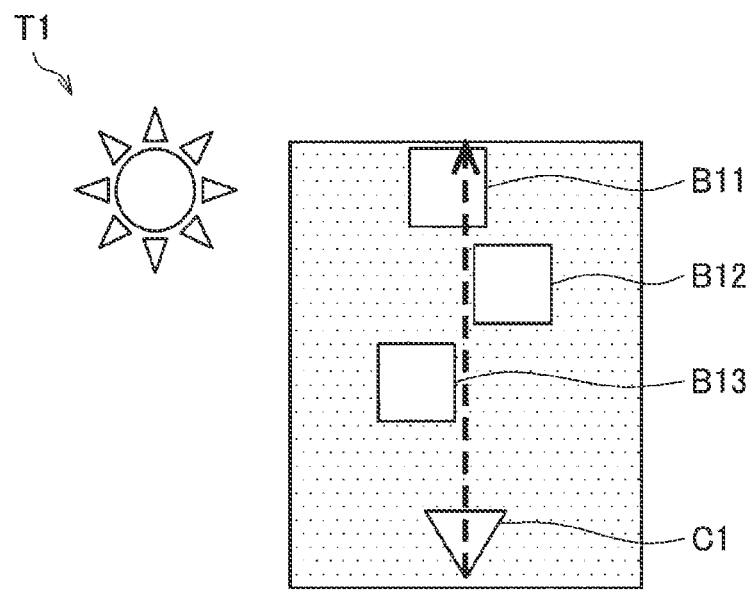
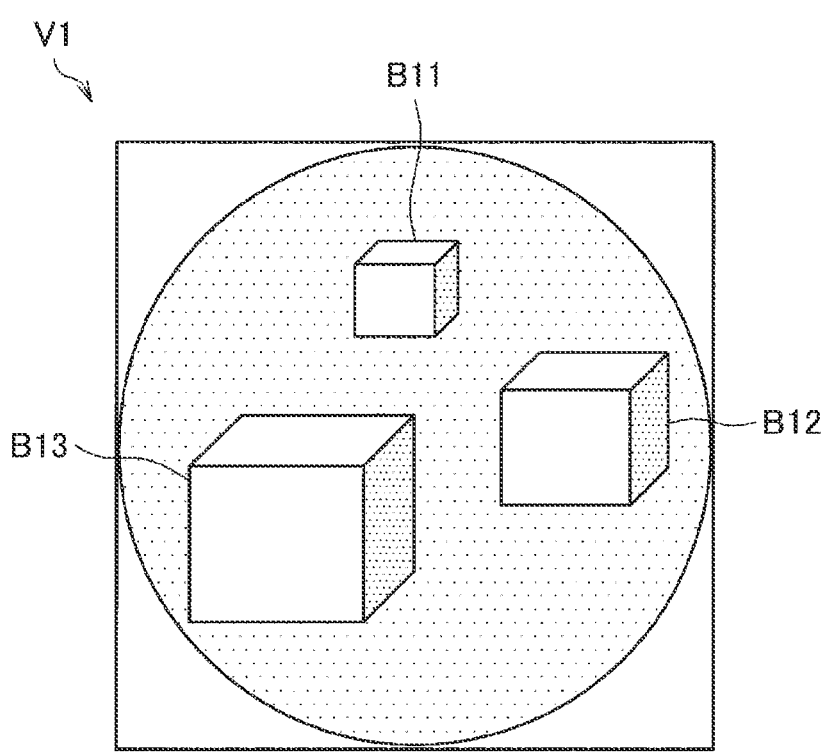

FIG. 6
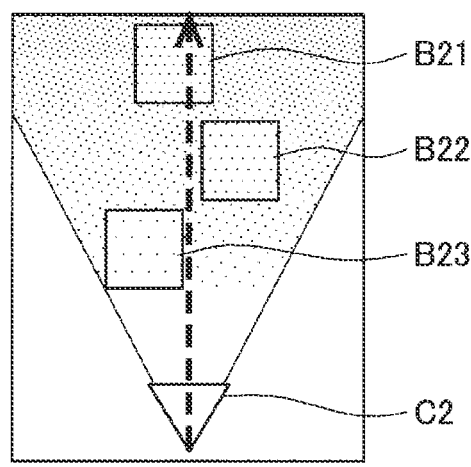
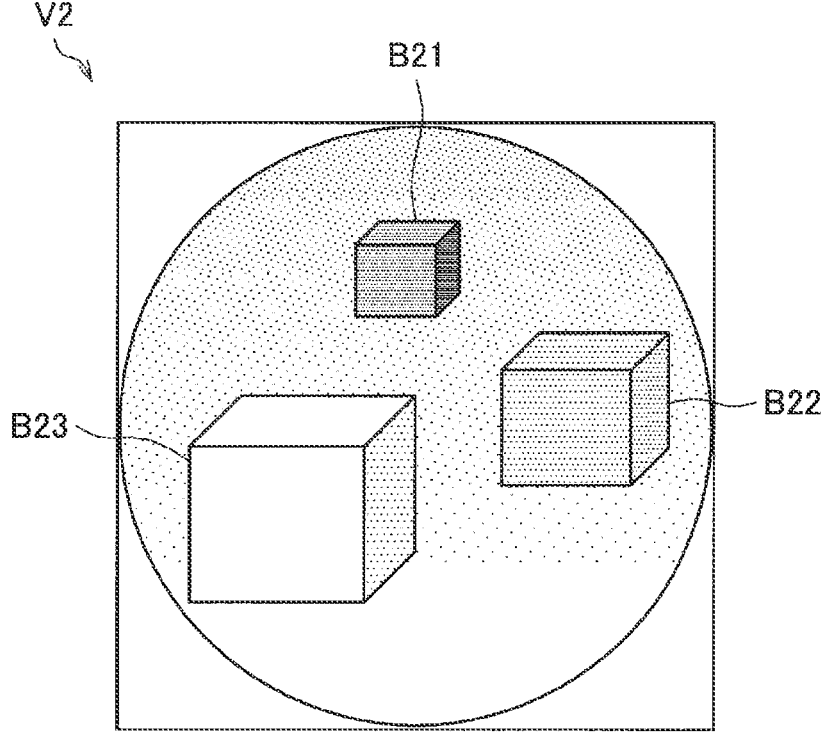

FIG. 15
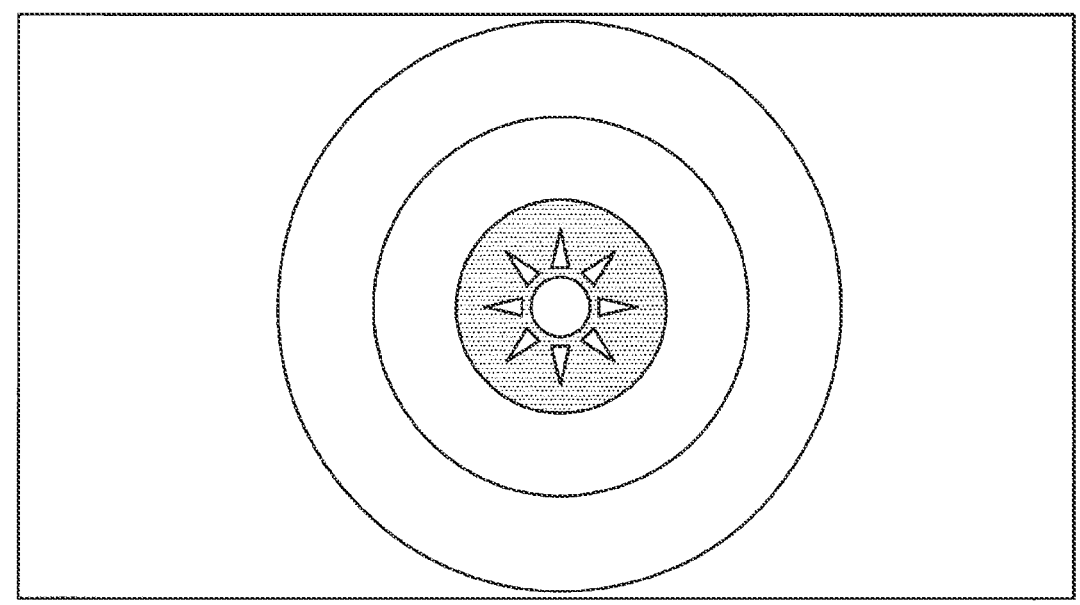
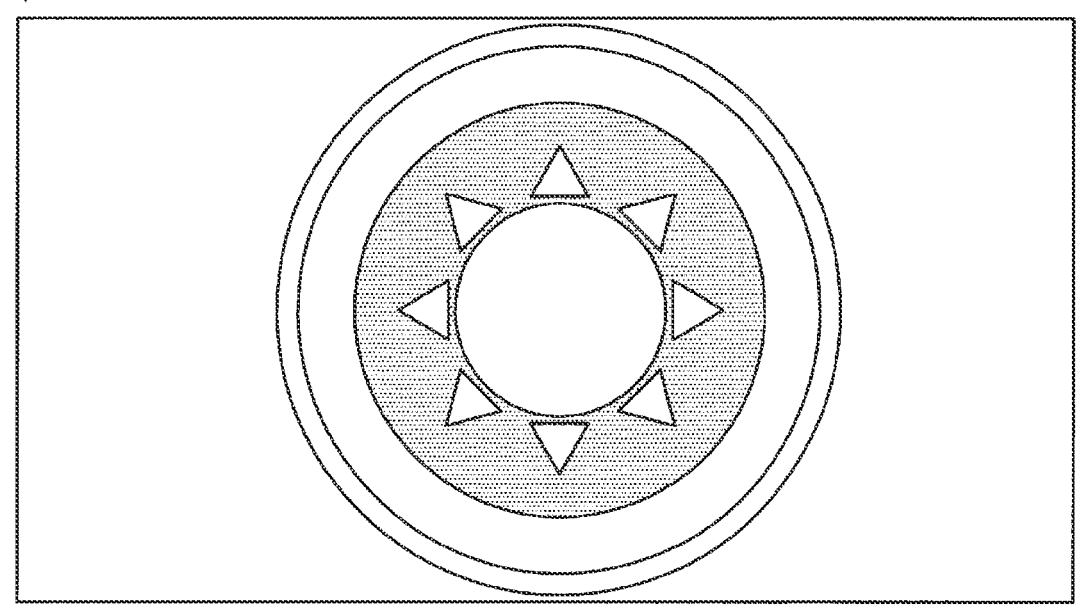

MEDICAL IMAGE PROCESSING DEVICE AND IMAGE PROCESSING METHOD

CROSS REFERENCE TO RELATED APPLICATIONS

This application is a U.S. National Phase of International Patent Application No. PCT/JP2017/026400 filed on Jul. 21, 2017, which claims priority benefit of Japanese Patent Application No. JP 2016-173378 filed in the Japan Patent Office on Sep. 6, 2016. Each of the above-referenced applications is hereby incorporated herein by reference in its entirety.

TECHNICAL FIELD

The present disclosure relates to a medical image processing device, an image processing method, and a program.

BACKGROUND ART

In medical systems such as an endoscopic surgery system, a plurality of monitors (display devices) has come to be used. In a system as described above, appropriately selecting a monitor on which an image is to be displayed and making the switch places a burden on a user. Therefore, Patent Literature 1, for example, discloses a medical system in which a monitor in accordance with the dimension of an input image is automatically selected and displayed.

CITATION LIST

Patent Literature

Patent Literature 1: JP 2016-36592A

DISCLOSURE OF INVENTION

Technical Problem

However, in the medical system as described above, a more flexible image display is demanded. For example, since the application of a monitor display varies in accordance with the role or situation of an individual user who uses the medical system, an image display in accordance with the application is demanded.

Solution to Problem

According to the present disclosure, there is provided a medical image processing device including: an acquisition unit configured to acquire application information indicating an application related to a display; and an image processing unit configured to perform image processing based on the application information to acquire an output image.

In addition, according to the present disclosure, there is provided an image processing method including: acquiring application information indicating an application related to a display; and performing, using a processor, image processing based on the application information to acquire an output image.

In addition, according to the present disclosure, a program causes a computer to achieve: a function of acquiring application information indicating an application related to a display; and a function of performing image processing based on the application information to acquire an output image.

Advantageous Effects of Invention

According to the present disclosure as described above, a more flexible image display is possible.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 5 is an explanatory diagram for describing the difference in brightness made by endoscope illumination and the extent of a dynamic range.

FIG. 6 is an explanatory diagram for describing the difference in brightness made by endoscope illumination and the extent of a dynamic range.

FIG. 15 is an explanatory diagram for describing image processing according to Variation 1.

MODE(S) FOR CARRYING OUT THE INVENTION

Figure 1:
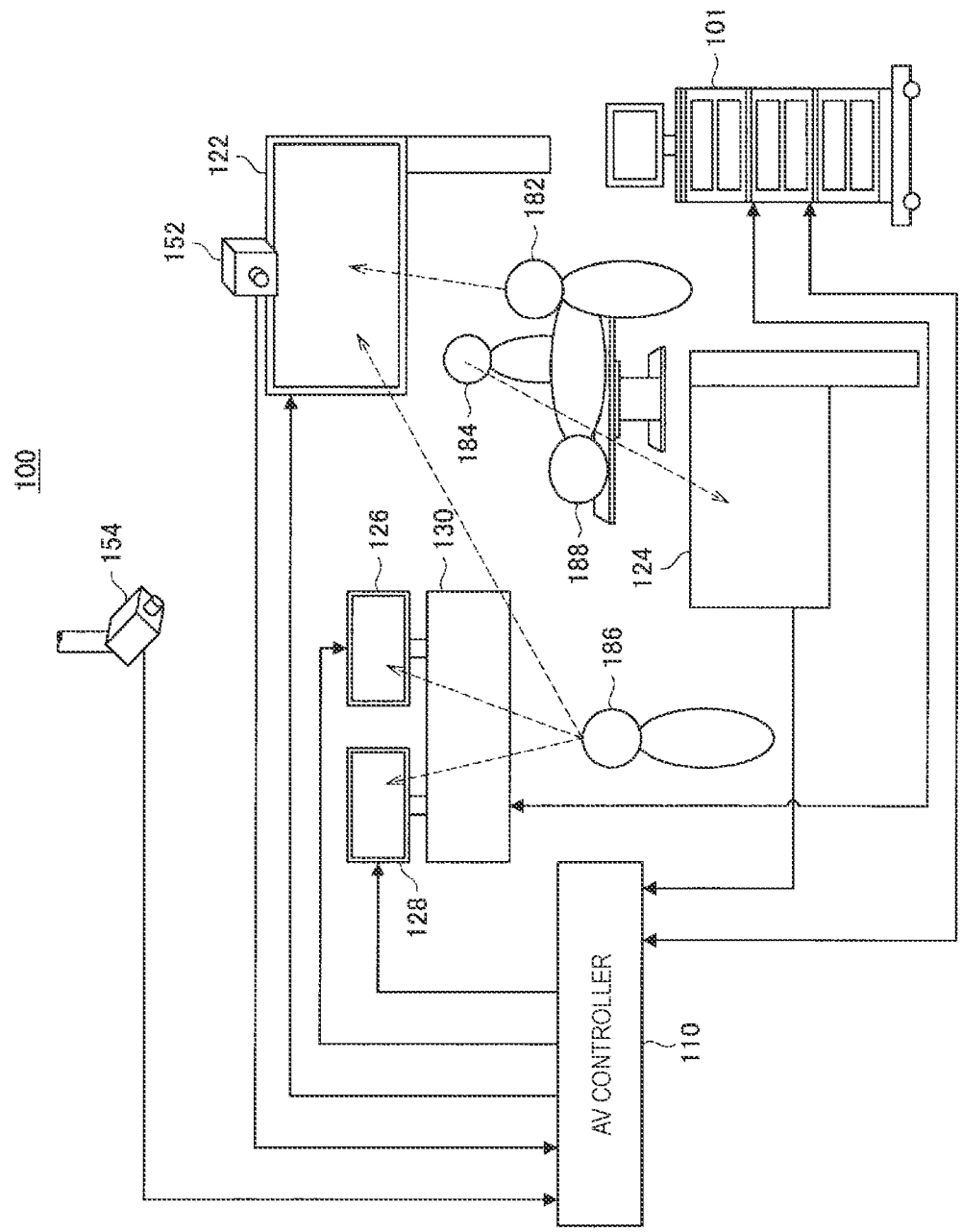
FIG. 1 is a diagram schematically showing an overall configuration of an operating room system 100 according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
<<1. Overview>>
<<2. Configuration>>
<<3. Operation>>
<<4. Variations>>
<<5. Hardware configuration example>>
<<6. Conclusion>>

1. Overview

First, a schematic configuration of an operating room system according to an embodiment of the present disclosure will be described with reference to FIG. 1.

FIG. 1 is a diagram schematically showing an overall configuration of an operating room system 100 according to an embodiment of the present disclosure. With reference to FIG. 1, the operating room system 100 is configured by connecting a group of devices installed in an operating room so as to be capable of cooperating with each other via an audio visual (AV) controller 110 (switcher).

Various devices may be installed in the operating room. FIG. 1 illustrates, as an example, a group of various devices 101 for endoscopic surgery, a plurality of monitors (an example of display devices) 122 to 128, vital information measuring equipment 130 that acquires vital information (an example of biological information) of a patient 188, a monitor camera 152 attached to the monitor 122, and a surgical field camera 154 provided at the ceiling of the operating room to image the general condition of the operating room.

The monitors 122 to 128 may have a 3D display function. In addition, the monitor camera 152 and the surgical field camera 154 may be stereo cameras capable of acquiring distance information.

Figure 2:
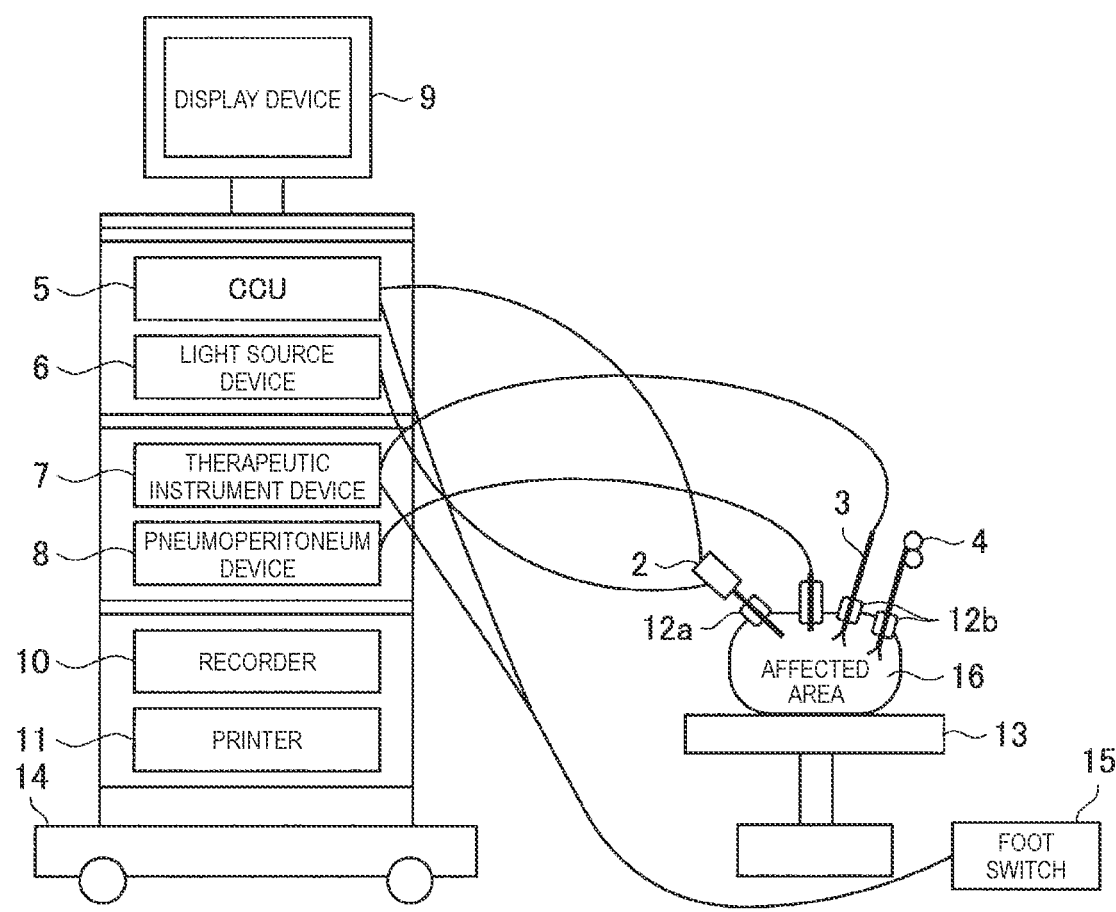
FIG. 2 is a diagram schematically showing a configuration of an endoscopic surgery system 1 according to the embodiment.

Here, among these devices, the group of devices 101 belongs to the endoscopic surgery system 1. FIG. 2 is a diagram schematically showing a configuration of the endoscopic surgery system 1.

In recent years, endoscopic surgeries are performed in the medical field instead of conventional laparotomies. For example, in the case where an abdominal surgery is performed, the endoscopic surgery system 1 arranged in an operating room as shown in FIG. 2 is used. Instead of opening the abdominal wall for laparotomy as conventional, hole opening instruments called trocars 12a, 12b are attached to the abdominal wall at several positions, and the endoscope 2, an energy therapeutic instrument 3, forceps 4, and the like are inserted into the body through holes provided in the trocars 12a, 12b. Then, video is captured by the endoscope 2 that images a living organism, and while watching an image of an affected area (a living organism such as a tumor) 16 displayed on a display device 9 in real time, a treatment such as resecting the affected area 16 with the energy therapeutic instrument 3 and the like is performed. The endoscope 2, the energy therapeutic instrument 3, and the forceps 4 are held by an operator, an assistant, an endoscopist (a manipulator of the endoscope), a robot, and the like.

A cart 14 on which devices for endoscopic surgery are mounted, a patient bed 13 for a patient to lay down, a foot switch 15, and the like are arranged in the operating room where such an endoscopic surgery is performed. Devices such as a camera control unit (CCU) 5, a light source device 6, a therapeutic instrument device 7, a pneumoperitoneum device 8, the display device 9, a recorder 10, and a printer 11, for example, are mounted on the cart 14 as medical equipment.

An image signal of the affected area 16 captured and acquired through an observation optical system of the endoscope 2 is transmitted to the CCU 5 via a camera cable, and after being subjected to signal processing in the CCU 5, output to the display device 9, so that an endoscopic image of the affected area 16 is displayed. Besides being connected to the endoscope 2 via a camera cable, the CCU 5 may also be connected wirelessly.

The light source device 6 is connected to the endoscope 2 via a light guide cable, and can switch light of various wavelengths for emission to the affected area 16. The therapeutic instrument device 7 is a high-frequency output device that outputs a high-frequency current to the energy therapeutic instrument 3 that cuts the affected area 16 using electrical heating, for example. The pneumoperitoneum device 8 is a device that includes air sending and air suction means, and sends air to the abdominal region, for example, in the body of the patient. The foot switch 15 controls the CCU 5, the therapeutic instrument device 7, and the like using a foot manipulation performed by an operator, an assistant, or the like as a trigger signal.

Respective devices belonging to the endoscopic surgery system 1 described above and the vital information measuring equipment 130 shown in FIG. 1 are also referred to as medical equipment. On the other hand, the monitors 122 to 128, the monitor camera 152, and the surgical field camera 154 are devices provided for the operating room, for example, and are also referred to as non-medical equipment.

In recent years, a twofold improvement in spatial resolution related to monitors (for example, the monitors 122 to 128) or an imaging device (for example, the endoscope 2) used in the medical field as described above is being made in each of the vertical and horizontal directions in such a form as SD, HD, 4K resolution, and 8K resolution in conformity with the broadcasting standard. Hereinafter, an example in which the endoscope 2 is an imaging device capable of imaging with the 8K resolution, and the monitors 122 to 128 are display devices capable of making a display with the 4K resolution will be described as an example.

The AV controller 110 exerts centralized control over processing concerning image displays in medical equipment and non-medical equipment. For example, the AV controller 110 may transmit images captured by the monitor camera 152 and the surgical field camera 154 to the group of devices 101 belonging to the endoscopic surgery system 1. In addition, the AV controller 110 may cause images captured by the endoscope 2 belonging to the endoscopic surgery system 1 to be displayed on the monitors 122 to 128. Note that control over an image display exerted by the AV controller 110 is not limited to the foregoing, but acquisition of an image from each device connected to the AV controller 110 and a display of an image on each device may be controlled in various ways.

Figure 3:
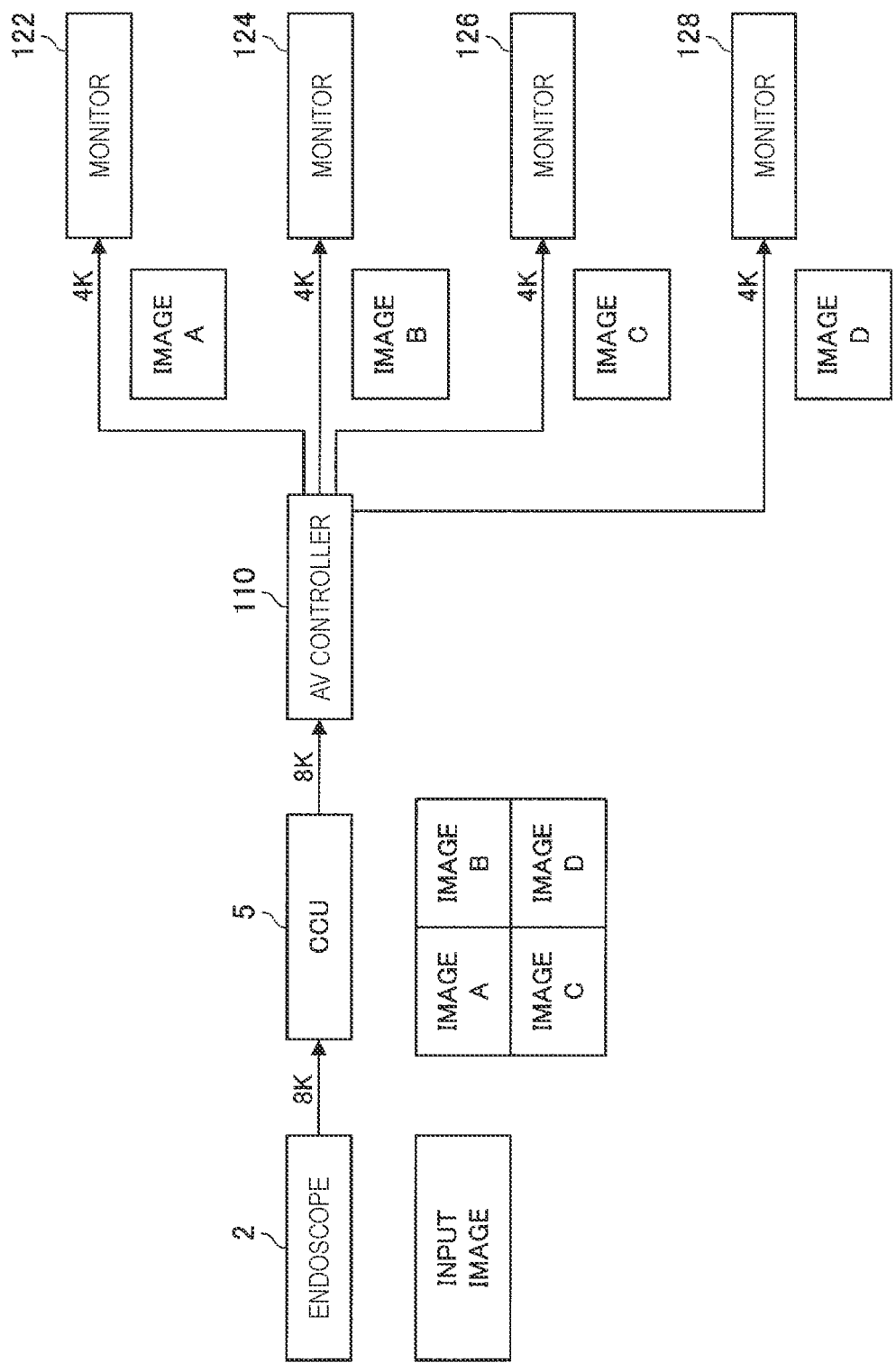
FIG. 3 is an explanatory diagram showing an example of display control exerted by an AV controller 110 according to the embodiment.

FIG. 3 is an explanatory diagram showing an example of display control exerted by the AV controller 110 according to the present embodiment. As shown in FIG. 3, an input image (INPUT IMAGE) with the 8K resolution acquired by the endoscope 2 is input to the CCU 5. The CCU 5 generates images (IMAGEs A to D) with the 4K resolution to be displayed on the monitors 122 to 128 from the input image.

Image processing for the CCU 5 to generate images with the 4K resolution will be described later.

As shown in FIG. 3, the CCU 5 may output (transmit) a plurality of images with the 4K resolution in combination as an image with the 8K resolution to the AV controller 110, or may output each of the plurality of images with the 4K resolution independently.

The AV controller 110 distributes the images acquired from the CCU 5 to the monitors 122 to 128. The AV controller 110 may exert control so as to distribute images (IMAGEs A to D) of predetermined four areas with the 8K resolution obtained by combining the plurality of images with the 4K resolution to the monitors 122 to 128, respectively, as shown in FIG. 3, for example.

Here, images that should be displayed on the monitors 122 to 128 may vary depending on the application in accordance with the role or situation of an individual user in the operating room system. For example, in a medical team in which an attending doctor such as a surgeon in charge of a surgery, an assistant such as a surgery assistant, an endoscopist, and an anesthesiologist, and a paramedic, that is, medical personnel such as a nurse and a clinical engineer utilize a plurality of monitors, information and granularity of the information required in accordance with an individual role may vary.

For example, for a surgeon in charge of a surgery who carries out a sophisticated surgical method, a high spatial resolution and a sense of immersion with respect to a surgical site and objects of interest such as a suture and a needle will be important. In addition, for a surgery assistant, a bird's eye field of view for becoming aware of the position of a surgical tool that he/she manipulates and the state of a living organism such as an organ held by the surgical tool may be more important than a sense of immersion. In addition, for a nurse, it is important to grasp the progress state of a surgery for the purpose of timing handing over of instruments and the like, and on the other hand, consideration for patient information, such as vital information (an example of biological information) of a patient, that cannot be acquired only from camera images is also important. In addition, for a clinical engineer, consideration for an influence exerted on the surgery by the state of equipment, for example, an insufflation device and an energy device that he/she manages is important. In addition, paramedics such as a nurse and a clinical engineer may not necessarily require an image resolution of a level that a doctor or the like requires.

In addition, since a user (user watching a monitor) related to a monitor display may change depending on a surgical method or progress or situation of a surgery, it is difficult and not preferable to manage all the monitors in association with users.

For example, in the example shown in FIG. 1, an attending doctor user (who may hereinafter simply be referred to as an attending doctor) 182 utilizes the monitor 122, and an assistant (who may hereinafter simply be referred to as an assistant or an assistant doctor) user 184 utilizes the monitor 124. However, the attending doctor user 182 and the assistant user 184 may change in position depending on the situation of a surgery, and in such a case, the monitors that the attending doctor user 182 and the assistant user 184 utilize may also change. In addition, a nurse user 186 may selectively use the monitors 122, 126, and 128 in accordance with the situation of the surgery.

Therefore, the operating room system 100 according to an embodiment of the present disclosure has been created using the above-described circumstances as a viewpoint. By acquiring an application related to a display and performing image processing in accordance with the application, the endoscopic surgery system 1 according to the present embodiment can achieve an image display in accordance with the application that changes depending on progress or situation of a surgery. Hereinafter, a configuration of the present embodiment having such effects will be described in detail.

2. Configuration

Hereinafter, configuration examples of the CCU 5 and the AV controller 110 included in the operating room system 100 according to an embodiment of the present disclosure will be described sequentially with reference to FIG. 4 to FIG. 10.

<2-1. Configuration of CCU>

Figure 4:
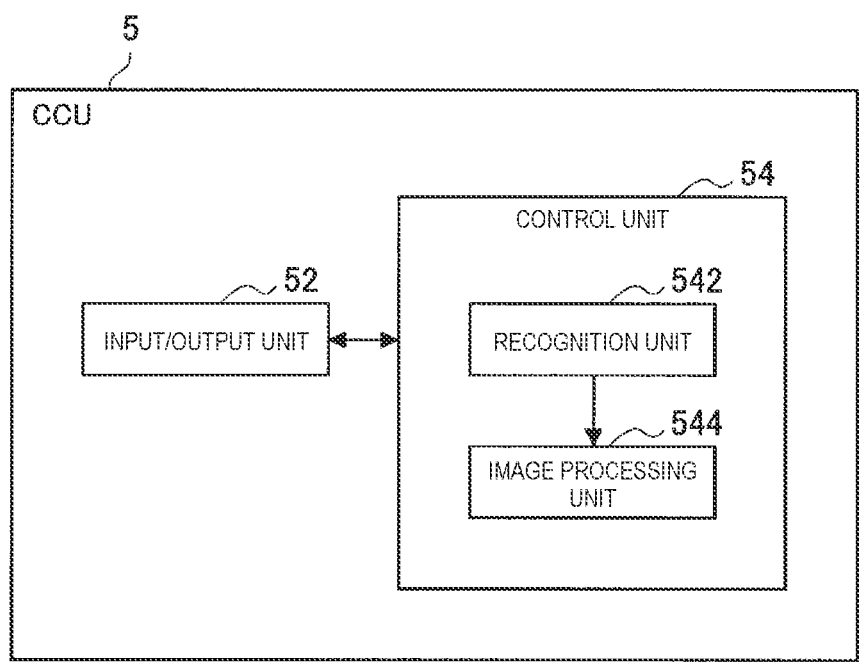
FIG. 4 is a block diagram showing a functional configuration example of a camera control unit (CCU) 5 according to the embodiment.

FIG. 4 is a block diagram showing a functional configuration example of the camera control unit (CCU) 5 according to the present embodiment. As shown in FIG. 4, the CCU 5 is a medical image processing device including an input/output unit 52 and a control unit 54.

The input/output unit 52 is connected to the AV controller 110 and the vital information measuring equipment 130 shown in FIG. 1, for example, and the endoscope 2, the foot switch 15, and the like described with reference to FIG. 2, and performs input/output of various signals and information.

For example, images captured by the monitor camera 152, the surgical field camera 154, and the endoscope 2 may be input to the input/output unit 52. In addition, vital information (an example of biological information) of a patient measured by the vital information measuring equipment 130 may be input to the input/output unit 52. In addition, information about a display device (the monitors 122 to 128, or the like) connected to the AV controller 110 may be input to the input/output unit 52. The information about a display device may include the resolution with which output can be made, the position of the display device, and the size of the display device, for example. In addition, in the case where the display device is previously associated with a user (for example, in the case where the display device is a terminal that a specific user holds, in the case where the display device is a wearable device such as a head mount display that the specific user wears, or the like), information about a display device may include information about an associated user. In addition, in the case where the display device is a display device dedicated to a specific application, information about a display device may include application information indicating the application.

In addition, the input/output unit 52 outputs an image signal related to an output image to be displayed on a display device to the AV controller 110. An output image may be output in association with a display device on which the output image should be displayed, or may be output in a manner included in a predetermined region of an image of larger size than the output image, as shown in FIG. 3. Such a configuration allows the AV controller 110 to distribute output images to the respective display devices.

The control unit 54 exerts control over the CCU 5 as a whole. In addition, the control unit 54 according to the present embodiment also functions as a recognition unit 542 and an image processing unit 544, as shown in FIG. 4.

The recognition unit 542 performs various types of recognition processing. In addition, the recognition unit 542 also functions as an acquisition unit that acquires application information indicating the application related to a display.

For example, the recognition unit 542 may acquire application information for each display device.

The application information may be an "attending doctor use" indicating that an attending doctor utilizes the display, an "assistant use" indicating that an assistant utilizes the display, a "medical personnel use" indicating that another member of medical personnel utilizes the display, or the like, for example. In addition, the application information may be a "manager use" indicating that a manager outside the operating room, rather than medical personnel in the operating room, utilizes the display. Note that the application information is not limited to the above-described examples, but may include information indicating a more detailed user action and an application in accordance with the situation of a surgery, for example.

The recognition unit 542 may acquire application information on the basis of recognition of a user related to a display, for example. For example, on the basis of images acquired from the monitor camera 152 and the surgical field camera 154, the recognition unit 542 may recognize the standing position, face orientation, line of sight, and the like of a person detected from the images to recognize a user of a display device related to a display. For example, in the example shown in FIG. 1, in the case where the line of sight of the attending doctor 182 directed to the monitor 122 is detected, a user of the monitor 122 may be recognized as the attending doctor 182, and in such a case, the recognition unit 542 may acquire application information called the "attending doctor use".

With such a configuration, since the application is automatically recognized, and a display in accordance with the application may be produced, a user does not need to perform an action for switching displays of a display device or switching image display destinations (display devices).

Note that the role (attending doctor, assistant, another member of medical personnel, or the like) of a user may be recognized by the recognition unit 542 from an action of the user, for example, or the role of the user may be acquired by previously associating the role of each user and individual identification information (for example, the face or the like). In addition, the role of the user may be acquired by having each user wear a device, a marker, or the like for recognition and using information about the device or the marker.

In addition, in the case where a plurality of persons has been recognized as users of an identical display device, the recognition unit 542 may acquire application information on the basis of priorities of roles previously set. For example, higher priorities may be set in the order of attending doctor, assistant, another member of medical personnel.

Note that recognition of a user and acquisition of application information performed by the recognition unit 542 is not limited to the above-described example. For example, the recognition unit 542 may recognize a user on the basis of recognition processing of user voice acquired from a voice input device such as a microphone not shown or an input (interrupt manipulation) from an input device such as the foot switch 15 shown in FIG. 2.

In addition, application information may be acquired on the basis of information about a display device related to a display. For example, in the case where information about a user associated with a display device is included in information about the display device, application information may be acquired on the basis of the information about the user. In addition, the recognition unit 542 may acquire application information on the basis of a combination of the above-described recognition of a user and information about the user included in the information about the display device. For example, in the case where a display device has been associated with another member of medical personnel, but a user of the display device recognized by line-of-sight recognition of the user is the attending doctor, the recognition unit 542 may acquire application information called the "attending doctor use".

In addition, application information may be acquired on the basis of the place of a display device, the position of the display device, or the transmission (distribution) destination of images. For example, in the case where a display device related to a display is a main monitor existing in the operating room, the recognition unit 542 may acquire application information called the "attending doctor use". In addition, in the case where the destination of images transmitted by the AV controller 110 is external to the operating room, the recognition unit 542 may acquire application information called the "manager use".

The above-described acquisition of application information is an example, and is not limited to the foregoing. For example, the recognition unit 542 may acquire application information on the basis of recognition of an action of the user, recognition of the surgery situation, or the like.

In addition, the recognition unit 542 may specify the position of interest (point of interest) to which the user pays attention from an input image which is an endoscopic image acquired from the endoscope 2.

For example, the recognition unit 542 may acquire a user manipulated position, and may specify the position of interest on the basis of the user manipulated position. For example, the recognition unit 542 may detect or track to acquire the user manipulated position from an input image, and may specify the manipulated position as the position of interest. For example, the recognition unit 542 may recognize a surgical tool manipulated by the user by an object recognition technology, and may recognize the leading end of the surgical tool as the manipulated position. For example, the recognition unit 542 may use an action of the user checking the orientation of a suture needle (an example of the surgical tool) (for example, an action of closing the suture needle) as a trigger to detect the suture needle, and may start tracking the suture needle.

In addition, the recognition unit 542 may detect or track to acquire the user manipulated position from an image acquired from the monitor camera 152 or the surgical field camera 154, and may specify the position corresponding to the manipulated position in the input image as the position of interest.

In addition, the recognition unit 542 may recognize the line of sight of the user related to a display from an image acquired from the monitor camera 152 or the surgical field camera 154, and may specify the position of interest on the basis of the line of sight. For example, the recognition unit 542 may specify the position in the input image corresponding to the line of sight position of the user in an image displayed on a display device, as the position of interest.

The image processing unit 544 performs image processing based on application information using an input image which is an endoscopic image acquired from the endoscope 2 as a target (input) to acquire an output image. Hereinafter, as an example of image processing based on application information performed by the image processing unit 544, image processing performed in the case where application information called the "attending doctor use", the "assistant use", and the "medical personnel use" has been acquired by the recognition unit 542 will be described sequentially.

First, the example in which the "attending doctor use" has been acquired as application information will be described.

In the case where the "attending doctor use" has been acquired as application information, the image processing unit 544 may perform processing of cutting out a region of interest from an input image which is an endoscopic image. For example, the image processing unit 544 may cut out a region with a predetermined resolution centering on the position of interest from an input image as the region of interest, or may cut out a region with a predetermined resolution centering on the central position of the input image as the region of interest. Note that the above-described predetermined resolution may be a resolution (for example, 4K resolution) with which the display device can produce a display.

With such a configuration, in an image acquired with a high resolution (for example, 8K resolution), an important region to which the user is paying attention may be cut out still with the high spatial resolution to be presented to the user.

A display of an image obtained by the processing of cutting out the region of interest as described above is particularly effective for an attending doctor user such as a surgeon in charge of a surgery, a main observer, or the like. For example, even a user who always gazes endoscopic images during a surgery does not necessarily require a sense of sharpness of images in the case of observing the surgical field from a broad view, performing a grasping manipulation, and the like. On the other hand, since what is important for the surgeon in charge of a surgery or the like who will perform sophisticated manipulations such as suturing and membrane detachment is a sense of definition of image information, the surgeon in charge of a surgery or the like may wish to gaze at a certain specific part of interest, rather than the whole angle of view captured by the endoscope 2. In such a case, it is common to attempt to enlarge an image by bringing the endoscope 2 closer to a target of interest or bringing the target of interest closer to the endoscope 2, that is, reducing the distance between a camera and a subject. However, such a manipulation is not preferable because the surgical field is narrowed, and an unintentional damage to an affected area due to a blind manipulation of an insert, such as an endoscope or forceps, or a complication may occur. On the other hand, if captured images can be displayed with a high spatial resolution, it is not necessarily required to perform a physical enlarging manipulation as described above, so that the above-described risks can be reduced.

Subsequently, the example in which the "assistant use" has been acquired as application information will be described. In the case where the "assistant use" has been acquired as application information, the image processing unit 544 may perform pixel addition processing of adding pixel values of a plurality of pixels in an input image to calculate the pixel value of a pixel in an output image. For example, through pixel addition processing of adding pixel values of four pixels adjacent horizontally and vertically in an input image captured with the 8K resolution to calculate the pixel value of a pixel in an output image, it is possible to acquire (downconvert) an output image with the 4K resolution.

An output image with the 4K resolution obtained by the pixel addition processing as described above has a higher signal noise (SN) ratio and more improved visibility than an output image with the 4K resolution obtained by simply performing downconversion (reduction processing).

An output image with the 4K resolution obtained by the pixel addition processing as described above is expected to be advantageous particularly for users such as a surgery assistant and an endoscopist who place importance on a bird's eye field of view. FIG. 5 and FIG. 6 are explanatory diagrams for describing the difference in brightness made by endoscope illumination and the extent of a dynamic range.

In a natural environment T1 shown in FIG. 5, objects B11 to B13 having an identical reflectance are radiated uniformly with light of the sun or the like. Note that an arrow of the broken line shown in FIG. 5 indicates a line-of-sight direction of a camera C1. As shown in FIG. 5, in an image V1 acquired by the camera C1, the objects B11 to B13 have the same brightness regardless of the distance from the camera C1.

In an endoscopic imaging environment T2 shown in FIG. 6, objects B21 to B23 having an identical reflectance are radiated nonuniformly by a light source that the endoscope C2 has. Note that an arrow of the broken line shown in FIG. 6 indicates a line-of-sight direction of the endoscope C2 and the illumination direction. As shown in FIG. 6, in an image V2 acquired by the endoscope C2, the objects B21 to B23 differ in brightness depending on the distance from the endoscope C2.

That is, in endoscopic imaging, an image having a very wide dynamic range is acquired because illuminance changes depending on the distance between a light source and a subject. In the example shown in FIG. 6, the object B21 is overexposed, and highlight clipping at a bright section occurs, and the object B23 is underexposed, and shadow clipping at a dark section may occur. Such shadow clipping and highlight clipping significantly reduce the visibility in observation.

Although it is also possible to increase the display intensity of a dark section having a low SN ratio by image processing such as gain correction processing or gamma correction processing, noise becomes noticeable, and in addition, information concerning a position where highlight clipping occurs is missing.

Therefore, in the situation where a sense of definition is not required in a sophisticated manipulation or the like, the effect in which the visibility of an endoscopic image is largely improved by increasing the sensitivity and dynamic range per pixel by the above-described pixel addition processing even if the spatial resolution is reduced can be expected.

Note that it is preferable to increase the quantization accuracy per pixel by pixel addition processing as described above, but the SN ratio of an image may be improved by reducing noise dispersion without changing the quantization accuracy by pixel averaging processing instead of the pixel addition processing. With such a configuration, it is possible to reduce the data size.

Subsequently, the example in which the "medical personnel use" has been acquired as application information will be described. In the case where the "medical personnel use" has been acquired as application information, the image processing unit 544 may generate an output image for causing a reduced input image obtained by carrying out downconversion (reduction processing) on an input image and additional information to be visually recognized at the same time. For example, the image processing unit 544 may perform processing of superimposing additional information on a reduced input image.

The additional information may include, for example, vital information (an example of biological information) such as the blood pressure, oxygen saturation, electrocardiogram of the patient, acquired by the vital information measuring equipment 130 described with reference to FIG. 1. Note that the additional information is not limited to the foregoing, but may include information indicating the state of various devices (for example, an insufflation device, an energy device, and the like), for example.

In the case where the additional information is image information, the image processing unit 544 may superimpose the additional information on a reduced input image in the form of Picture in Picture (PinP). In addition, in the case where the additional information is text information, the image processing unit 544 may render the additional information in a predetermined font to be superimposed on the reduced input image.

As described above, visually recognizing the reduced input image and the additional information at the same time will be effective particularly for paramedic users other than doctors, for example. For example, for medical personnel such as a nurse and a clinical engineer, the sense of definition and overall visibility of an endoscopic image are not so important, but the display is utilized rather for grasping the situation necessary for handing over instruments to a doctor during a surgery and checking and managing medical equipment and patient state. Thus, a user as described above always needs to pay attention not only to endoscopic images but also to various types of equipment, and it is desirable that information is united integrally to the extent possible.

Thus, when vital information such as the blood pressure, oxygen saturation, and electrocardiogram of a patient, for example, and an endoscopic image having a resolution of the extent that enables the state of equipment or a surgical tool to be observed are displayed on one display device, the effect of reducing burdens on the above-described user can be expected.

Note that the image processing unit 544 may perform simple downconversion (for example, sub-sampling processing) on an input image, or may perform downconversion by interpolation, or may perform downconversion by the above-described pixel addition processing or pixel averaging processing.

In addition, the image processing unit 544 may generate an output image by aligning an image obtained by downconverting an input image to be less than the display resolution of a display device and additional information, instead of superimposing the additional information.

An example of image processing based on application information performed by the image processing unit 544 has been described above. Note that image processing based on application information performed by the image processing unit 544 is not limited to the above-described examples, but various types of image processing may be assumed in accordance with acquired application information.

In addition, the image processing unit 544 further performs development processing including de-mosaicing processing, gain correction processing, gamma correction processing, and the like. For example, the image processing unit 544 may perform development processing after the above-described image processing based on application information. In the case where the image size (resolution) is reduced by image processing based on application information as described above, the processing amount can be reduced in some cases by performing development processing after image processing based on application information.

<2-2. Configuration of AV Controller>

Figure 7:
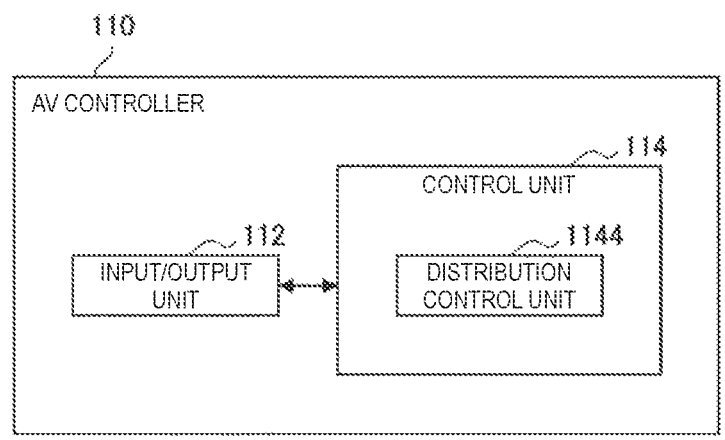
FIG. 7 is a block diagram showing a functional configuration example of the AV controller 110 according to the embodiment.

Subsequently, a configuration example of the AV controller 110 will be described with reference to FIG. 7. FIG. 7 is a block diagram showing a functional configuration example of the AV controller 110 according to the present embodiment. As shown in FIG. 7, the AV controller 110 is a medical image processing device including an input/output unit 112 and a control unit 114.

The input/output unit 112 is connected to the medical equipment and non-medical equipment shown in FIG. 1, and performs input/output of various signals and information.

For example, images captured by the monitor camera 152, the surgical field camera 154, and the endoscope 2 may be input to the input/output unit 112. In addition, information on a display device (the monitors 122 to 128, or the like) may be input to the input/output unit 112. In addition, an image signal from the CCU 5 may be input to the input/output unit 112.

The control unit 114 exerts control over the AV controller 110 as a whole. In addition, the control unit 114 according to the present embodiment also functions as a distribution control unit 1144 as shown in FIG. 7.

The distribution control unit 1144 controls a distribution destination (output destination) of a signal and information input by the input/output unit 112. For example, the distribution control unit 1144 may distribute an image signal input from the CCU 5 to the monitors 122 to 128 as described with reference to FIG. 3.

3. Operation

A configuration example of the present embodiment has been described above. Subsequently, an operation example of the present embodiment will be described with reference to FIG. 8 to FIG. 12. First, overall processing of the present embodiment will be described with reference to FIG. 8, and then, application recognition processing will be described with reference to FIG. 9, and image processing in accordance with respective applications will be described with reference to FIG. 10 to FIG. 12.

Figure 8:
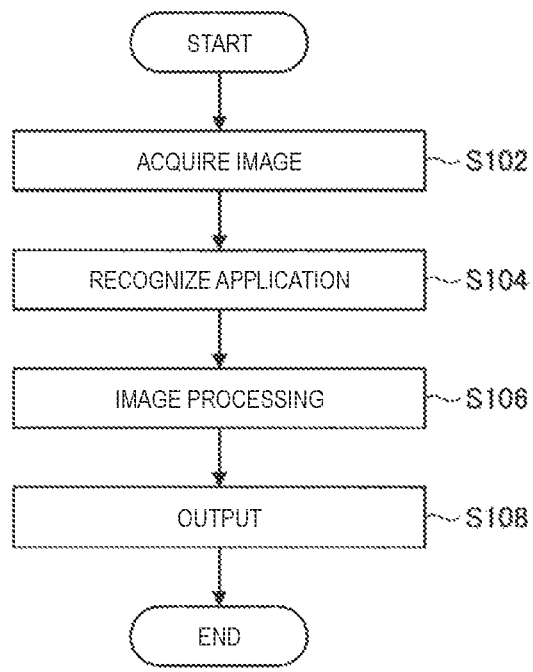
FIG. 8 is a flowchart diagram showing overall processing according to the embodiment.

FIG. 8 is a flowchart diagram showing overall processing of the present embodiment. As shown in FIG. 8, first, the CCU 5 acquires an input image captured by the endoscope 2 and images captured by the monitor camera 152 and the surgical field camera 154 (S102).

Subsequently, the recognition unit 542 of the CCU 5 recognizes the application of each display device to acquire application information (S104). An example of application recognition processing will be described later with reference to FIG. 9.

Subsequently, the image processing unit 544 of the CCU 5 performs image processing on the input image on the basis of the acquired application information to generate an output image (S106). Subsequently, the output image or an image signal related to the output image is output from the input/output unit 52 of the CCU 5 (S108).

Figure 9:
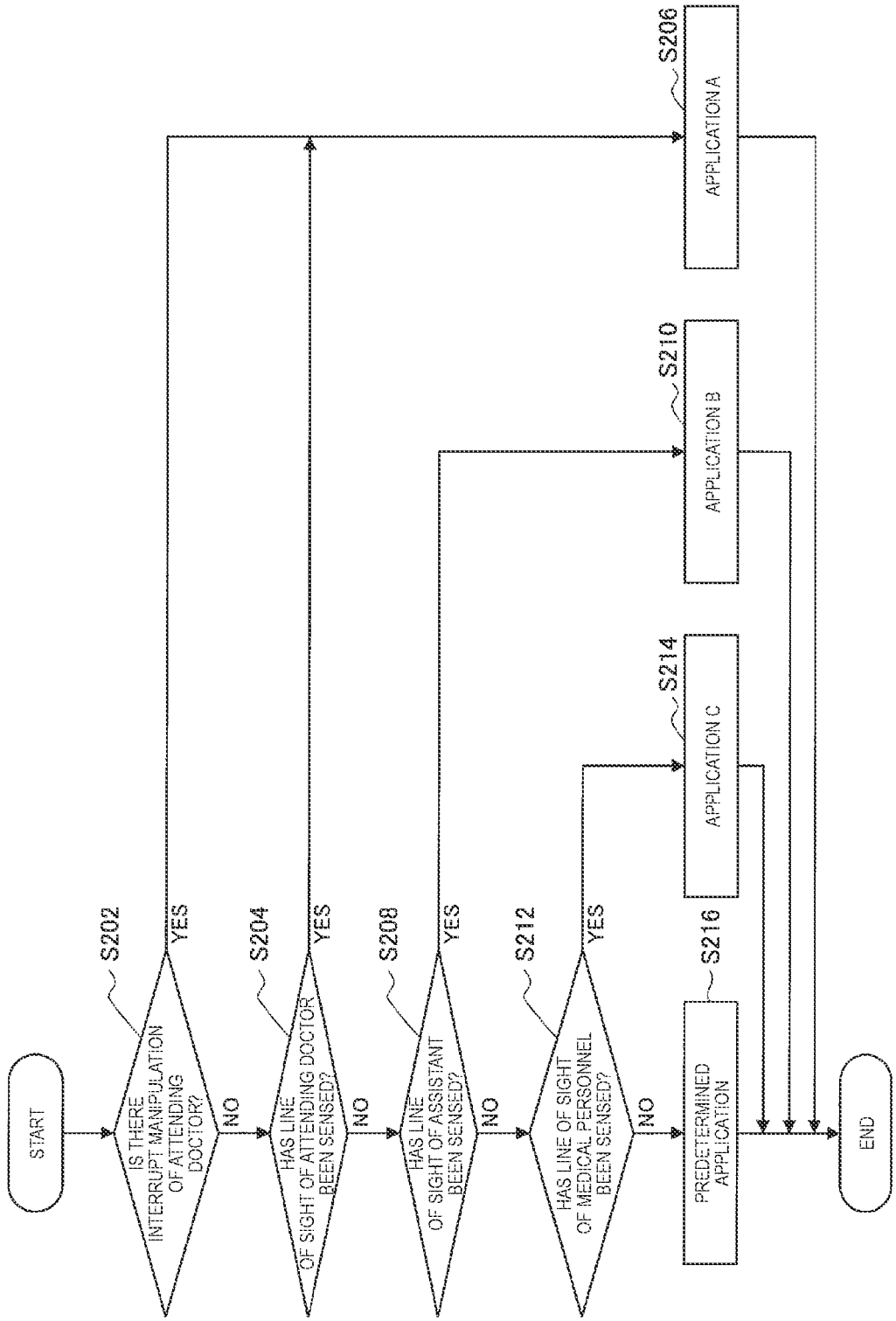
FIG. 9 is a flowchart diagram showing an example of application recognition processing performed by a recognition unit 542 according to the embodiment.

Overall processing of the present embodiment has been described above. Subsequently, an example of the application recognition processing in the above-described step S104 will be described with reference to FIG. 9. FIG. 9 is a flowchart diagram showing an example of the application recognition processing performed by the recognition unit 542. Note that, in the example shown in FIG. 9, an application A indicates that application information to be acquired is the "attending doctor use", an application B indicates that application information to be acquired is the "assistant use", and an application C indicates that application information to be acquired is the "medical personnel use".

As shown in FIG. 9, it is first determined whether or not there is an interrupt manipulation (a voice input, a manipulation of the foot switch 15, or the like) of an attending doctor (S202). In the case where there is an interrupt manipulation of the attending doctor (YES in S202), or in the case where there is no interrupt manipulation of the attending doctor, but the line of sight of the attending doctor to a display device has been sensed (NO in S202 and YES in S204), the "attending doctor use" is acquired as application information (S206).

Subsequently, in the case where the line of sight of the attending doctor has not been sensed, and the line of sight of an assistant doctor to the display device has been sensed (NO in S204 and YES in S208), the "assistant use" is acquired as application information (S210).

Subsequently, in the case where the line of sight of the assistant has not been sensed, and the line of sight of medical personnel other than the doctor to the display device has been sensed (NO in S204 and YES in S208), the "medical personnel use" is acquired as application information (S214).

In addition, in the case where the line of sight of medical personnel other than the doctor has not been sensed (YES in S212), predetermined application information having been previously set is acquired (S216). Note that the predetermined application information is set for each display device, for example, and may be included in information about the display device.

The recognition processing of application information has been described above. Note that processing in the above-described steps S202 to S216 may be repeated at any time or at predetermined time intervals.

In addition, in the case where new application information related to a certain display device (a first display device) has been changed from previous application information, the previous application information may be acquired as application information about another display device (a second display device) for which the new application information has been acquired. With such a configuration, since, in the case where application information related to the first display device has been changed, information having been displayed on the first display device before the point of time is displayed continuously on the second display device, it is possible for a user requiring the information, if exists, to continuously acquire the information.

Subsequently, respective processes performed in the case where the "attending doctor use", the "assistant use", and the "medical personnel use" have been acquired as application information will be described with reference to FIG. 10 to FIG. 12.

Figure 10:
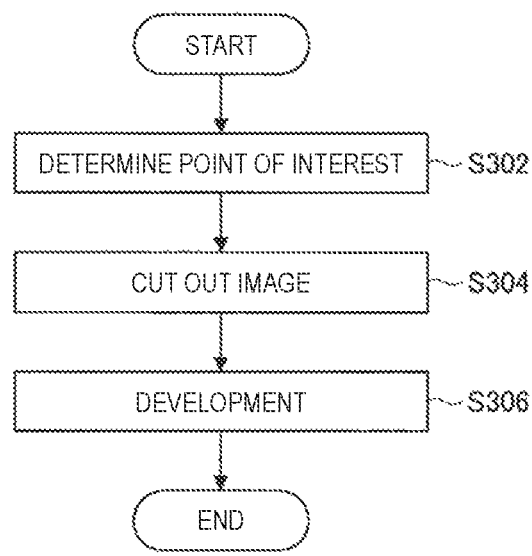
FIG. 10 is a flowchart diagram showing an example of image processing in the case where an "attending doctor use" has been acquired as application information.

FIG. 10 is a flowchart diagram showing an example of image processing in the case where the "attending doctor use" has been acquired as application information. As shown in FIG. 10, first, the recognition unit 542 determines a position of interest (point of interest) to which a user pays attention (S302). Subsequently, the image processing unit 544 performs processing of cutting out a region of interest based on the position of interest from an input image (S304). Subsequently, the image processing unit 544 performs development processing (S306).

Figure 11:
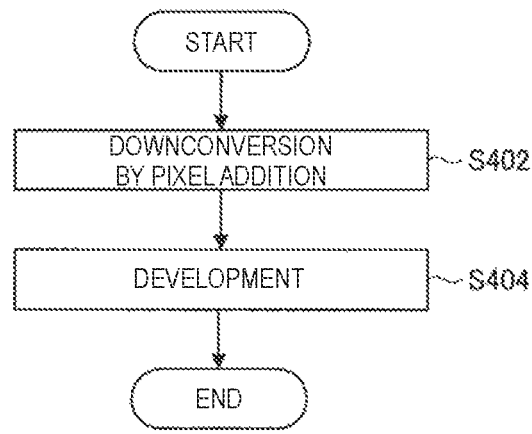
FIG. 11 is a flowchart diagram showing an example of image processing in the case where an "assistant use" has been acquired as application information.

FIG. 11 is a flowchart diagram showing an example of image processing in the case where the "assistant use" has been acquired as application information. As shown in FIG. 11, first, the image processing unit 544 performs downconversion by pixel addition on an input image (S402). Subsequently, the image processing unit 544 performs development processing (S404).

Figure 12:
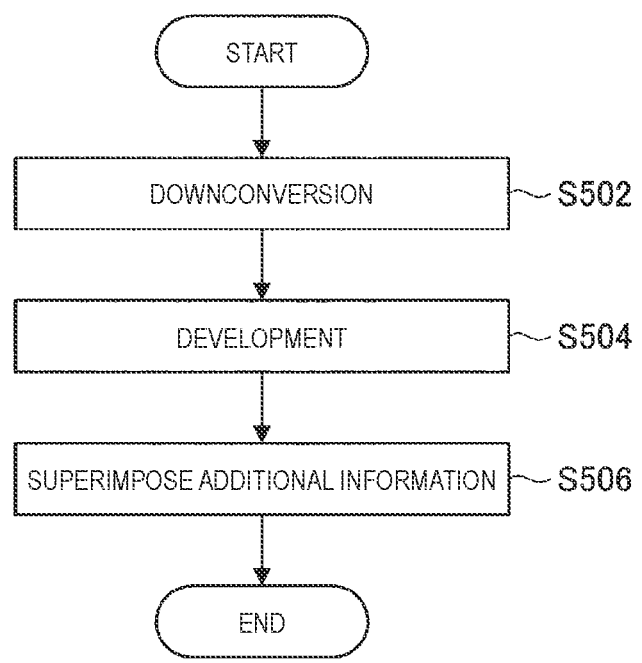
FIG. 12 is a flowchart diagram showing an example of image processing in the case where a "medical personnel use" has been acquired as application information.

FIG. 12 is a flowchart diagram showing an example of image processing in the case where the "medical personnel use" has been acquired as application information. As shown in FIG. 12, first, the image processing unit 544 performs downconversion on an input image (S502). Subsequently, the image processing unit 544 performs development processing (S504). Further, the image processing unit 544 performs processing of superimposing additional information on an image obtained by the development processing in step S504 (S506).

4. Variations

An embodiment of the present disclosure has been described above. Hereinafter, some variations of the present embodiment will be described. Note that the respective variations which will be described below may be applied to the present embodiment individually, or may be applied to the present embodiment in combination. In addition, each of the variations may be applied instead of the configuration described in the present embodiment, or may be additionally applied to the configuration described in the present embodiment.

<4-1. Variation 1>

The above-described embodiment describes the example in which the image processing unit 544 performs processing of cutting out a region of interest from an input image in the case where the "attending doctor use" has been acquired as application information, whilst the present embodiment is not limited to such an example. For example, the image processing unit 544 may perform processing of mixing pixels of images having different resolutions obtained from an input image to acquire an output image, instead of the processing of cutting out a region of interest. Hereinafter, such an example will be described as Variation 1.

Figure 13:
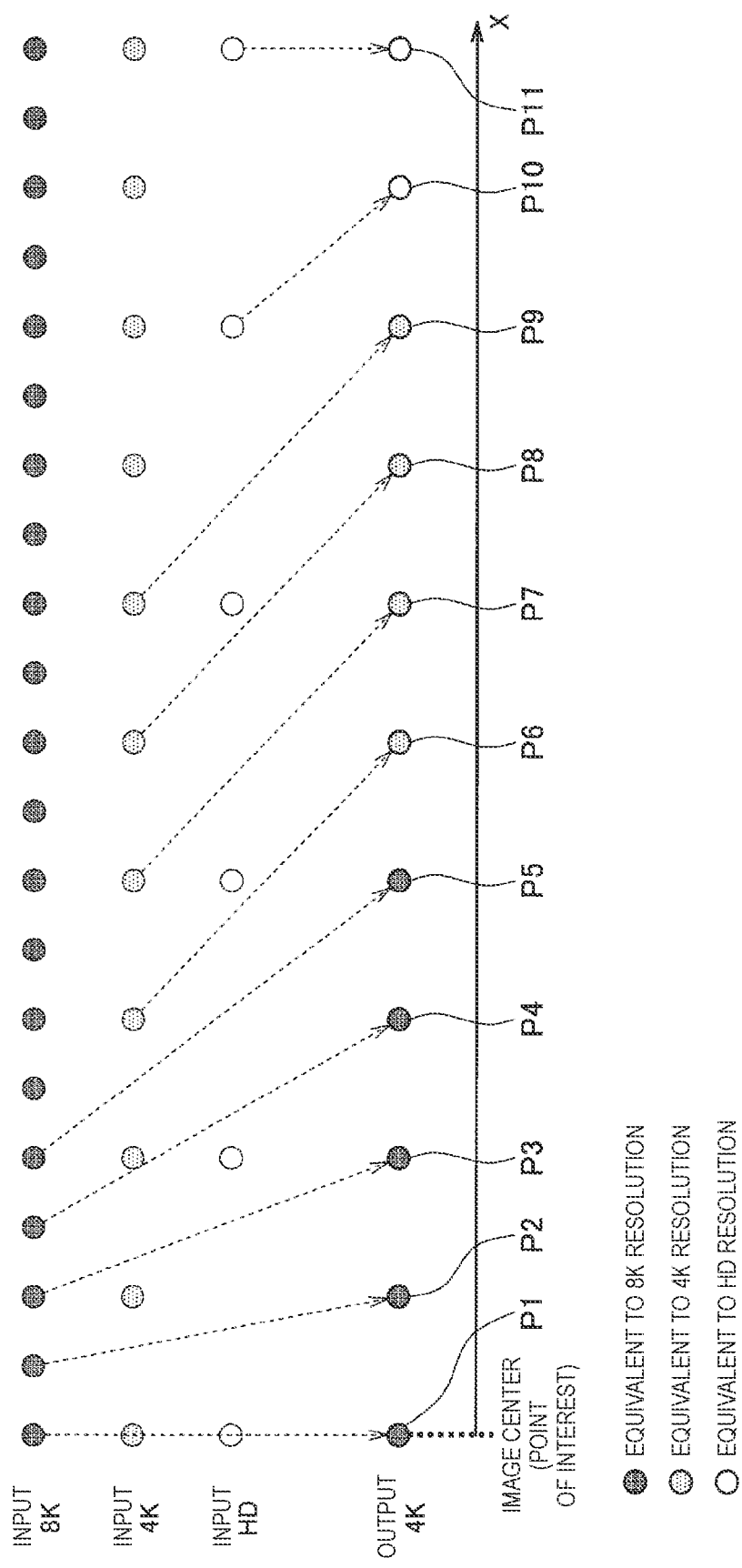
FIG. 13 is an explanatory diagram for describing image processing according to Variation 1.
Figure 14:
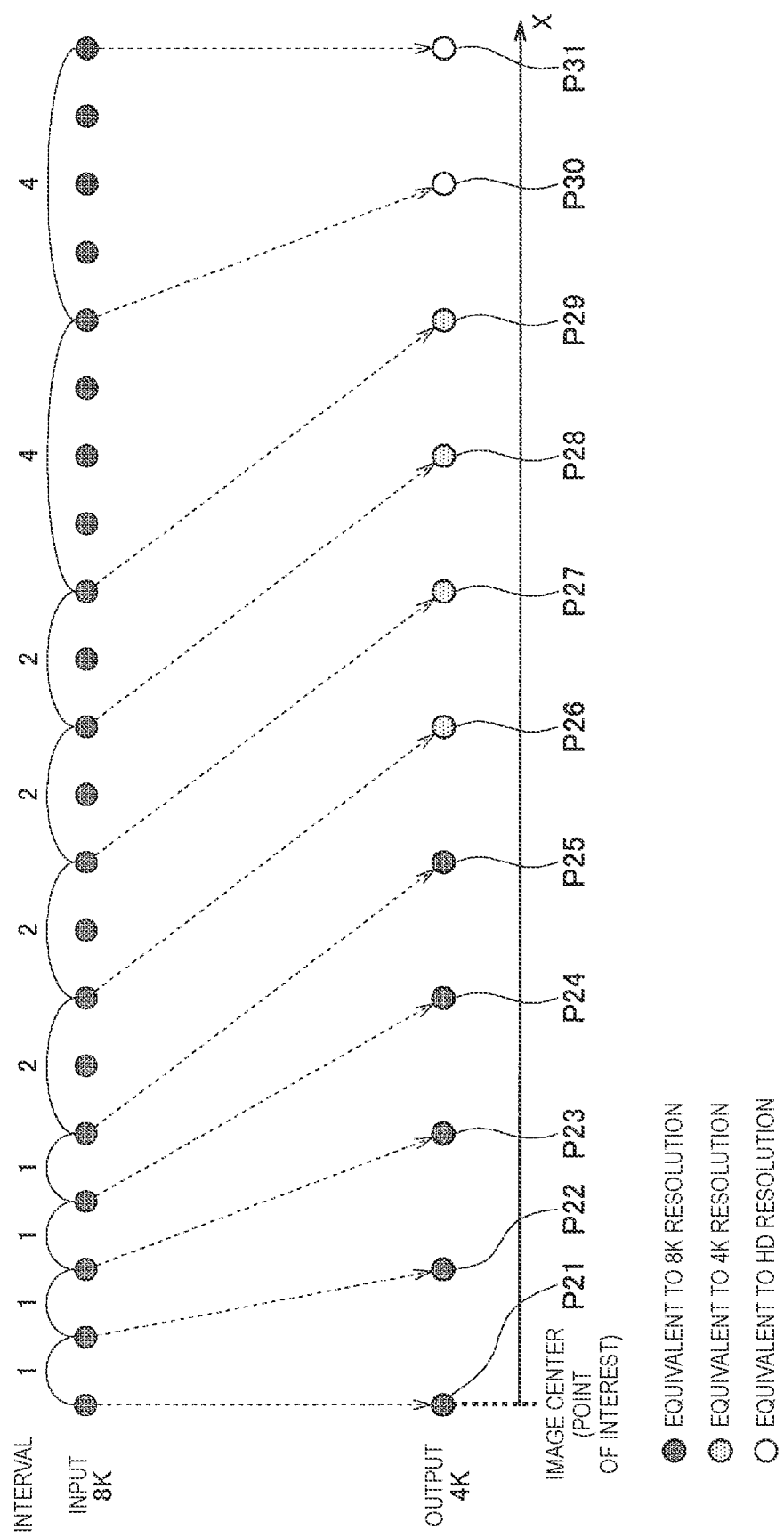
FIG. 14 is an explanatory diagram for describing image processing according to Variation 1.

FIG. 13 to FIG. 15 are explanatory diagrams for describing image processing according to the present variation. The image processing unit 544 according to the present variation performs downconversion processing on an input image with the 8K resolution) to generate an image with the 4K resolution and an image with the HD resolution. Further, the image processing unit 544 according to the present variation generates (acquires) an output image using the input image with the 8K resolution, the image with the 4K resolution, and the image with the HD resolution such that pixels of an image having a higher resolution are used with an approach to the position of interest. Hereinafter, processing in which the image processing unit 544 according to the present variation specifies the pixel value of each pixel of an output 4K (output image with the 4K resolution) using an input 8K (input image with the 8K resolution), an input 4K (image with the 4K resolution), and an input HD (image with the HD resolution) will be described with reference to FIG. 13. Note that FIG. 13 shows only some pixels in each image taken out for ease of description. In addition, FIG. 13 shows an example in which a point of interest (position of interest) is the central position of an input image for simplicity, whilst the position of interest is not limited to such an example, but may be specified variously by the recognition unit 542 as described above.

First, as shown in FIG. 13, a predetermined number of pixels in the input 8K positioned close to the point of interest (position of interest) are referred to, and pixel values of pixels P1 to P5 in the output 4K are specified in the order closer to the point of interest. Subsequently, a predetermined number of pixels of the input 4K farther from the point of interest than the position of a pixel of the input 8K corresponding to the pixel P5 farthest from the point of interest among pixels already specified are sequentially referred to, and pixel values of pixels P6 to P9 in the output 4K are specified. Subsequently, pixels of the input HD farther from the point of interest than the position of a pixel of the input 4K corresponding to the pixel P9 farthest from the point of interest among pixels already specified are sequentially referred to, and pixel values of pixels P10, P11 in the output 4K are specified.

Note that the number of pixels referred to in the input 8K may be determined by a ratio of using the input 8K to the number of pixels of the output 4K previously set. For example, if pixels of the input 8K are used for all the pixels in the output 4K, the input size does not fall within the range of the output size, so that output and input are adjusted to agree with each other in the coordinate relationship by referring some pixels in the input 4K and the input HD as described above. Thus, the number of pixels to be referred to in the input 4K and the number of pixels to be referred to in the input HD may also be specified by the ratio of using the input 8K to the number of pixels of the input 4K.

By generating an output image as described above, a subject closer to the position of interest may be displayed in a larger manner.

In addition, it is also possible to generate an output image having similar properties directly from an input image with the 8K resolution without generating an image with the 4K resolution or an image with the HD resolution. Such a method will be described with reference to FIG. 14.

With distance from the point of interest as shown in FIG. 14, the interval of pixels to be referred to in the input 8K (input image) is increased, so that the resolution perceived from pixels in the output 4K (output image) is reduced. For example, the pixel values of pixels P21 to P25 referred to with the interval between pixels in the input 8K being 1 are perceived as being equivalent to the 8K resolution. In addition, the pixel value of pixels P26 to P29 referred to with the interval between pixels in the input 8K being 2 are perceived as being equivalent to the 4K resolution. In addition, the pixel values of pixels P30, P31 referred to with the interval between pixels in the input 8K being 4 are perceived as being equivalent to the HD resolution. Note that the pixel value in the output 4K may be a value obtained by directly referring to the input 8K as described above, or may be a value calculated by linear interpolation or the like.

By generating an output image by a method described with reference to FIG. 13 or FIG. 14, a subject closer to the position of interest may be displayed in a larger manner. FIG. 15 is a schematic view showing an image of an output image obtained by the above-described image processing. An image G22 shown in FIG. 15 is an image obtained by simply downconverting an input image. An image G24 shown in FIG. 15 is an output image obtained by the image processing described with reference to FIG. 13 or FIG. 14. As shown in FIG. 15, in the image G24, a subject closer to the image center (position of interest) may be displayed in a larger manner. Such a configuration allows the user to observe a subject closer to the position of interest with greater attention while taking a bird's eye view of the entire image.

<4-2. Variation 2>

Figure 16:
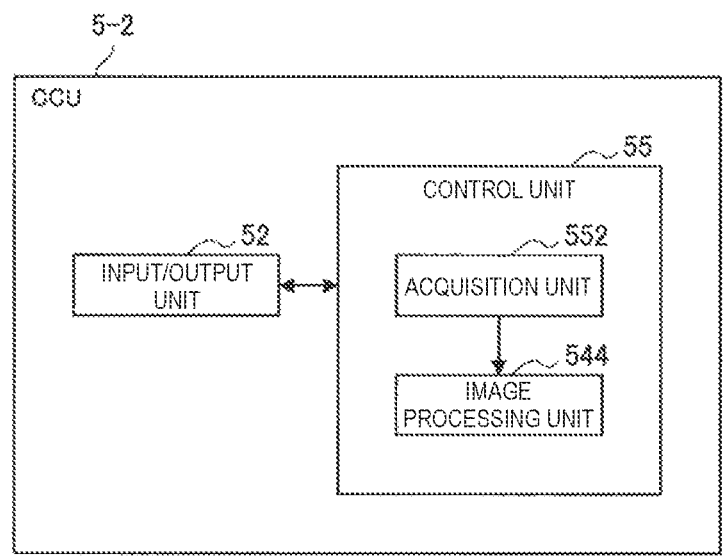
FIG. 16 is a block diagram showing a configuration example according to Variation 2.
Figure 17:
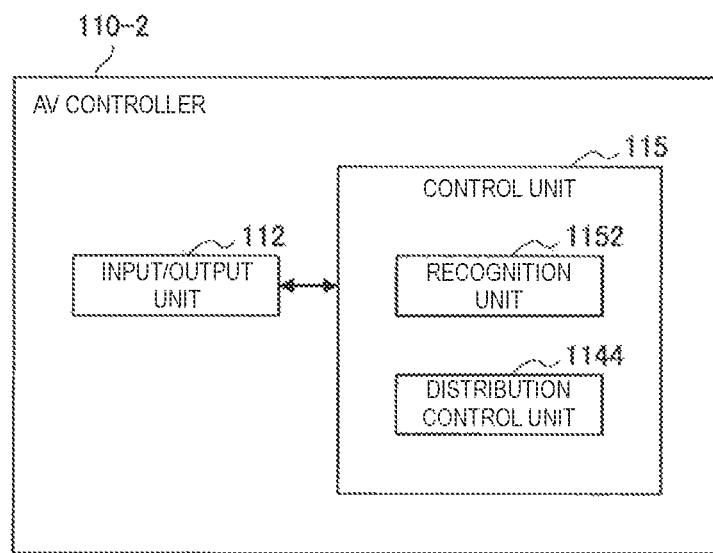
FIG. 17 is a block diagram showing a configuration example according to Variation 2.
Figure 18:
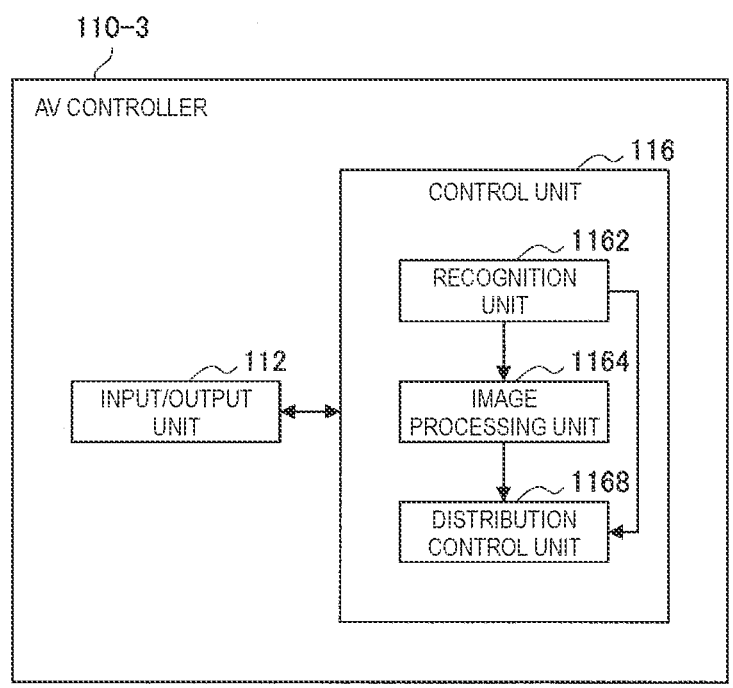
FIG. 18 is a block diagram showing a configuration example according to Variation 2.

The above-described embodiment describes a configuration example in which the CCU 5 performs application recognition processing and image processing in accordance with the application, whilst the present disclosure is not limited to such an example. Hereinafter, another configuration example will be described as Variation 2 with reference to FIG. 16 to FIG. 18. FIG. 16 to FIG. 18 are block diagrams showing a functional configuration example according to Variation 2.

FIG. 16 and FIG. 17 are block diagrams showing a functional configuration example of a CCU 5-2 and an AV controller 110-2 in the case where the AV controller performs the application recognition processing, and the CCU performs the image processing in accordance with the application.

As shown in FIG. 16, the CCU 5-2 differs from the CCU 5 in FIG. 4 in that the functional configuration of a control unit 55 partly differs from the functional configuration of the control unit 54 in FIG. 4. Note that identical reference characters are assigned to components substantially similar to the respective components shown in FIG. 4 among respective components shown in FIG. 16, and thus, description will be omitted.

An acquisition unit 552 shown in FIG. 16 acquires application information from the AV controller 110-2 which will be described later via the input/output unit 52, and provides the application information for an image processing unit 554.

As shown in FIG. 17, the AV controller 110-2 differs from the AV controller 110 in FIG. 7 in that the functional configuration of a control unit 115 partly differs from the functional configuration of the control unit 114 in FIG. 7. Note that identical reference characters are assigned to components substantially similar to the respective components shown in FIG. 7 among respective components shown in FIG. 17, and description will thus be omitted.

A recognition unit 1152 shown in FIG. 17 performs various types of recognition processing to recognize and acquire application information indicating the application related to a display, for example, similarly to the recognition unit 542 described with reference to FIG. 4. The application information acquired by the recognition unit 1152 is output from the input/output unit 112 to the CCU 5-2.

According to the above-described configuration, the transmission amount is suppressed since the AV controller 110-2 transmits the application information to the CCU 5-2, instead of information (for example, images captured by the monitor camera 152 and the surgical field camera 154) for recognizing the application.

In addition, it is also possible for the AV controller to perform application recognition processing and image processing in accordance with the application. FIG. 18 is a block diagram showing a functional configuration example of an AV controller 110-3 in the case where the AV controller performs the application recognition processing and the image processing in accordance with the application.

As shown in FIG. 18, the AV controller 110-3 differs from the AV controller 110-2 in FIG. 17 in that the functional configuration of a control unit 116 partly differs from the functional configuration of the control unit 115 in FIG. 6. Note that identical reference characters are assigned to components substantially similar to the respective components shown in FIG. 17 among respective components shown in FIG. 18, and description will thus be omitted.

A recognition unit 1162 performs various types of recognition processing to recognize and acquire application information indicating the application related to a display, for example, similarly to the recognition unit 1152 described with reference to FIG. 17. The application information acquired by the recognition unit 1162 is provided for an image processing unit 1164.

The image processing unit 1164 performs image processing based on the application on an input image input from the CCU to generate an output image, similarly to the image processing unit 544 described with reference to FIG. 4. Note that, in the case where development processing is performed by the CCU, the image processing unit 1164 does not need to perform development processing.

A distribution control unit 1168 controls a distribution destination (output destination) of a signal input by the input/output unit 112 and information, similarly to the distribution control unit 1144 described with reference to FIG. 7. Further, the distribution control unit 1168 distributes the output image generated by the image processing unit 1164 to a display device corresponding to the application information acquired by the recognition unit 1162.

5. Hardware Configuration Example

An embodiment and respective variations of the present disclosure have been described above. Information processing such as recognition processing and image processing performed by the control units 54, 55 described above is achieved by the cooperation between software and hardware of the CCU 5 (the CCU 5, the CCU 5-2) described below, for example.

Figure 19:
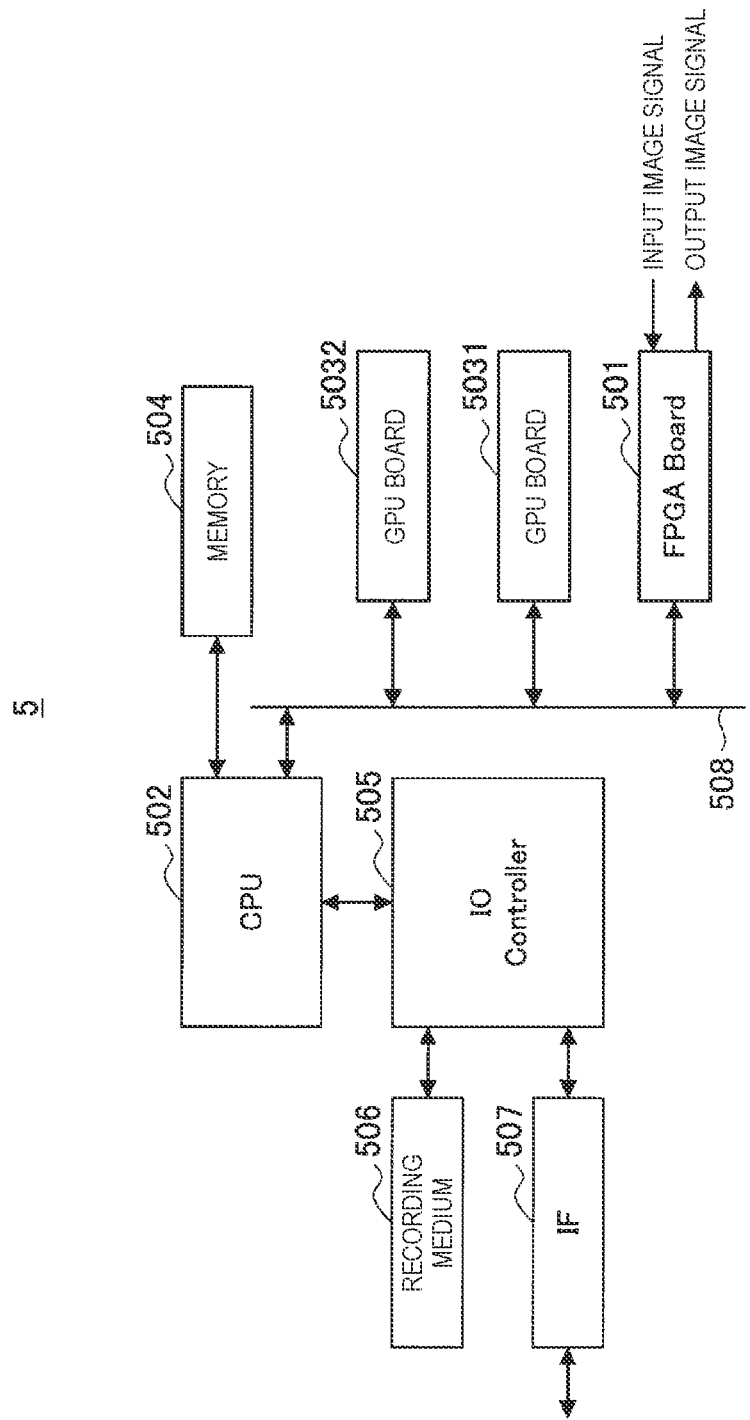
FIG. 19 is an explanatory diagram showing a hardware configuration example.

FIG. 19 is an explanatory diagram showing an example of a hardware configuration of the CCU 5. The CCU 5 includes an FPGA board 501, a CPU 502, GPU boards 5031, 5032, a memory 504, an IO controller 505, a recording medium 506, and an interface 507, for example. In addition, the FPGA board 501, the CPU 502, and the GPU boards 5031, 5032 are connected with a bus 508, for example. The FPGA board 501 includes an FPGA, an input interface in which an input image signal is input from the AV controller 110 or the endoscope 2, and an output interface from which an output image signal is output to the AV controller 110 or the display device 9, for example.

The CPU 502 and the GPU boards 5031, 5032 execute various types of software such as related software, for example, to perform various types of processing. The CPU 502 includes a processor. The GPU boards 5031, 5032 each include a graphics processing unit (GPU) and a dynamic random access memory (DRAM).

The memory 504 stores various types of data such as data corresponding to an input image signal and data corresponding to an output image signal, for example. The CPU 502 plays a role of controlling writing/reading of various types of data into/from the memory 504.

The CPU 502 divides image data stored in the memory 504 in accordance with data stored in the memory 504, processing capabilities of the GPU boards 5031, 5032, and contents of processing. Then, the GPU of each of the GPU boards 5031, 5032 carries out predetermined processing on supplied data upon division, and outputs a processing result to the CPU 502.

The IO controller 505 plays a role of controlling transmission of a signal between the CPU 502 and the recording medium 506 and the interface 507, for example.

The recording medium 506 functions as a storage unit (not shown) to store various types of data such as image data and various applications. Here, examples of the recording medium 506 include a solid state drive and the like. In addition, the recording medium 506 may be attachable/detachable to/from the CCU 5.

Examples of the interface 507 include a universal serial bus (USB) terminal and a processing circuit, a local area network (LAN) terminal, and a transmission/reception circuit, and the like.

Note that the hardware configuration of the CCU 5 is not limited to the configuration shown in FIG. 19. For example, FIG. 19 shows an example where there are two GPU boards 5031, 5032, whilst there may be two or more boards. In addition, in the case where the CPU 502 has the function of a GPU, the CCU 5 does not need to include the GPU boards 5031, 5032.

In addition, a hardware configuration of the CCU 5 has been described above, whilst the AV controller 110 (the AV controllers 110, 110-2, and 110-3) also has hardware equivalent to the CPU 502, the memory 504, and the like, similarly to the CCU 5. Then, a cooperation between the hardware of the AV controller 110 and software enables the functions of the control units 114, 115, and 116 to be achieved, for example. In addition, it is possible to manufacture a computer program for achieving the functions of the CCU 5 and the AV controller 110 according to the present embodiment as described above and to mount the computer program on a PC or the like. In addition, it is possible to provide a computer-readable recording medium in which such a computer program is stored. The recording medium is a magnetic disk, an optical disk, a magneto-optical disk, a flash memory, or the like, for example. In addition, the above-described computer program may be distributed via a network, for example, rather than using a recording medium.

6. Conclusion

According to an embodiment of the present disclosure as described above, since an image to be displayed is acquired by image processing based on application information acquired automatically, a more flexible image display is possible.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, image processing according to the present disclosure is not limited to the image processing described in the above embodiment. For example, image processing which will be described below may be performed.

For example, in the case where it is recognized by the recognition unit that an endoscope has been removed, image processing of reducing the frame rate may be performed. With the above-described configuration, it is possible to reduce the transmission amount and the processing amount.

In addition, in the case where it is determined by detection processing of an endoscope (camera) or the like that a low frequency component in an input image is dominant, image processing of downconverting to an image with a resolution lower than the maximum resolution with which the display device can produce a display may be performed. Note that reasons why a low frequency component in an input image is dominant include contamination, out-of-focus, and blurriness, and in such cases, it is considered that a user feels less uncomfortable even if an image with a lower resolution is displayed. With such a configuration, it is possible to reduce the transmission amount and the processing amount.

In addition, in the case where the intensity average value of an image is less than a predetermined value, pixel addition processing may be performed regardless of application information. With such a configuration, it is possible to cause an image improved in SN ratio to be displayed in the case where a dark image is acquired because of a low light amount, for example.

In addition, the image processing unit may perform conversion between a 2D image and a 3D image. For example, in the case where the "attending doctor use" has been acquired as application information, the image processing unit may convert an input image to a 3D image to acquire an output image. In addition, in the case where application information other than the "attending doctor use" has been acquired as application information, the image processing unit may acquire a 2D image as an output image. With such a configuration, it is possible to suppress the processing amount related to a monitor display for another user who does not require a high sense of immersion as compared to an attending doctor, while giving the attending doctor a sense of immersion.

In addition, in the case of distributing live video (real-time video) not targeted for a direct surgical manipulation to the outside of the operating room, the above-described types of image processing may be performed individually or in combination for the purpose of improving the transmission efficiency or for the purpose of improving the image quality.

In addition, in the case of distributing live video targeted for a direct surgical manipulation, such as a remote manipulation through use of a surgical robot, to the outside of the operating room, it is very important that the latency is low, so that image processing of reducing the resolution or frame rate may be performed, for example. With such a configuration, it is possible to reduce the transmission amount and the processing amount.

In addition, steps in the above-described embodiment are not necessarily be processed in time series along the order described as flowchart diagrams. For example, the respective steps in the processing of the above-described embodiment may be processed in an order different from the order described as flowchart diagrams, or may be processed in parallel.

In addition, the above-described embodiment describes an example in which the present technology is applied to a medical endoscope, whilst the present technology is not limited to such an example, but may be applied to various image processing devices.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical image processing device including:

an acquisition unit configured to acquire application information indicating an application related to a display; and an image processing unit configured to perform image processing based on the application information to acquire an output image.

(2)

The medical image processing device according to (1), in which the application information is acquired on the basis of recognition of a user related to the display.

(3)

The medical image processing device according to (1) or (2), in which the application information is acquired on the basis of information about a display device related to the display.

(4)

The medical image processing device according to any one of (1) to (3), in which the image processing performed by the image processing unit includes processing of cutting out a region of interest from an input image.

(5)

The medical image processing device according to (4), in which the region of interest is specified on the basis of a manipulated position of a user.

(6)

The medical image processing device according to (4), in which the region of interest is specified on the basis of a line of sight of a user related to the display.

(7)

The medical image processing device according to any one of (1) to (6), in which the image processing performed by the image processing unit includes pixel addition processing.

(8)

The medical image processing device according to any one of (1) to (7), in which the image processing performed by the image processing unit includes pixel averaging processing.

(9)

The medical image processing device according to any one of (1) to (8), in which the image processing performed by the image processing unit includes processing of superimposing additional information on an image.

(10)

The medical image processing device according to (9), in which the additional information includes biological information of a patient.

(11)

The medical image processing device according to any one of (1) to (10), in which the image processing performed by the image processing unit includes processing of mixing pixels of images having different resolutions obtained from an input image to acquire the output image.

(12)

The medical image processing device according to (11), in which the image processing unit acquires the output image such that pixels of an image having a higher resolution are used with an approach to a position of interest.

(13)

The medical image processing device according to (12), in which the position of interest is specified on the basis of a manipulated position of a user.

(14)

The medical image processing device according to (12), in which the position of interest is specified on the basis of a line of sight of a user related to the display.

(15)

The medical image processing device according to any one of (1) to (14), in which the application information includes at least any one of an attending doctor use, an assistant use, or a medical personnel use.

(16)

The medical image processing device according to any one of (1) to (15), in which the image processing performed by the image processing unit is processing targeted at an endoscopic image.

(17) An image processing method including:
acquiring application information indicating an application related to a display; and
performing, using a processor, image processing based on the application information to acquire an output image.

(18) A program for causing a computer to achieve:
a function of acquiring application information indicating an application related to a display; and
a function of performing image processing based on the application information to acquire an output image.

REFERENCE SIGNS LIST 1 endoscopic surgery system
2 endoscope
3 energy therapeutic instrument
4 forceps
5 camera control unit (CCU)
6 light source device
7 therapeutic instrument device
8 pneumoperitoneum device
9 display device
10 recorder
11 printer
52 input/output unit
54 control unit
100 operating room system
110 AV controller
112 input/output unit
114 control unit
130 vital information measuring equipment

The invention claimed is:

1. A medical image processing device, comprising:
circuitry configured to:
recognize a user of a display device among a plurality of users based on at least one of a position, a face orientation, or a line of sight of the user;
acquire application information that indicates an application related to a display, wherein the application information is acquired based on the recognition of the user of the display device; and
control the display device to switch an output image displayed on the display device, wherein the output image is switched based on the acquired application information.

2. The medical image processing device according to claim 1, wherein the circuitry is further configured to acquire the application information based on information about the display device related to the display.

3. The medical image processing device according to claim 1, wherein the circuitry is further configured to cut out a region of interest from an input image.

4. The medical image processing device according to claim 3, wherein the region of interest is specified based on a manipulated position of the user.

5. The medical image processing device according to claim 3, wherein the region of interest is specified based on the line of sight of the user related to the display.

6. The medical image processing device according to claim 1, wherein the circuitry is further configured to execute a pixel addition process.

7. The medical image processing device according to claim 1, wherein the circuitry is further configured to execute a pixel averaging process.

8. The medical image processing device according to claim 1, wherein the circuitry is further configured to superimpose additional information on an image displayed on the display device.

9. The medical image processing device according to claim 8, wherein the additional information comprises biological information of a patient.

10. The medical image processing device according to claim 1, wherein the circuitry is further configured to mix pixels of images that have different resolutions obtained from an input image to acquire the output image.

11. The medical image processing device according to claim 10, wherein the circuitry is further configured to acquire the output image such that pixels of an image that have a higher resolution are used with an approach to a position of interest.

12. The medical image processing device according to claim 11, wherein the position of interest is specified on based on a manipulated position of the user.

13. The medical image processing device according to claim 11, wherein the position of interest is specified based on the line of sight of the user related to the display.

14. The medical image processing device according to claim 1, wherein the application information comprises at least one of an attending doctor use, an assistant use, or a medical personnel use.

15. The medical image processing device according to claim 1, wherein the circuitry is further configured to execute an image process related to an endoscopic image.

16. The medical image processing device according to claim 1, wherein the circuitry is further configured to circuitry configured to recognize the user of the display device among the plurality of users based on a marker worn by the user.

17. The medical image processing device according to claim 1, wherein, in case where the plurality of users is recognized as users of the display device, the circuitry is further configured acquire the application information based on priorities of the plurality of users.

18. An image processing method, comprising:
recognizing, by a processor, a user of a display device among a plurality of users based on at least one of a position, a face orientation, or a line of sight of the user;
acquiring, by the processor, application information that indicates an application related to a display, wherein the application information is acquired based on the recognition of the user of the display device; and
controlling, by the processor, the display device to switch an output image displayed on the display device, wherein the output image is switched based on the acquired application information.

19. A non-transitory computer-readable medium having stored thereon, computer-executable instructions which, when executed by a computer, cause the computer to execute operations, the operations comprising:
recognizing a user of a display device among a plurality of users based on at least one of a position, a face orientation, or a line of sight of the user;
acquiring application information that indicates an application related to a display, wherein the application information is acquired based on the recognition of the user of the display device; and controlling the display device to switch an output image displayed on the display device, wherein the output image is switched based on the acquired application information.

* * * * *